US012779126B2

(12) United States Patent
Marici et al.

(10) Patent No.: US 12,779,126 B2
(45) Date of Patent: Nov. 3, 2026

(54) BRAKE TOWER WITH BIASING COMPONENTS AND MEDICAL INJECTION DEVICE INCLUDING THE SAME

(71) Applicant: Becton, Dickinson and Company, Franklin Lakes, NJ (US)

(72) Inventors: Paul Paia Marici, Piscataway, NJ (US); Stephen C. Simmons, Ringwood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 806 days.

(21) Appl. No.: 18/028,158

(22) PCT Filed: Sep. 23, 2021

(86) PCT No.: PCT/US2021/051690

§ 371 (c)(1),
(2) Date: Mar. 23, 2023

(87) PCT Pub. No.: WO2022/066863

PCT Pub. Date: Mar. 31, 2022

(65) Prior Publication Data

US 2023/0364347 A1 Nov. 16, 2023

Related U.S. Application Data

(60) Provisional application No. 63/083,617, filed on Sep. 25, 2020.

(51) Int. Cl.

*A61M 5/315* (2006.01)
*A61M 5/24* (2006.01)

(52) U.S. Cl.

CPC .... *A61M 5/31528* (2013.01); *A61M 5/31541* (2013.01); *A61M 5/31551* (2013.01); *A61M 5/31585* (2013.01); *A61M 2005/2407* (2013.01)

(58) Field of Classification Search

CPC .......... A61M 5/31525; A61M 5/31535; A61M 5/31541; A61M 5/31551; A61M 5/31561; A61M 5/31585; A61M 2005/2407; A61M 5/31528

See application file for complete search history.

(56) References Cited

U.S. PATENT DOCUMENTS

| | | | | |
|---|---|---|---|---|
| 9,421,334 | B2 | 8/2016 | Quinn et al. | |
| 2014/0046268 | A1 | 2/2014 | Quinn et al. | |
| 2014/0094765 | A1 | 4/2014 | Pala | |
| 2018/0177953 | A1 | 6/2018 | Quinn et al. | |
| 2019/0022332 | A1* | 1/2019 | Kohlbrenner ..... | A61M 5/31561 |

(Continued)

FOREIGN PATENT DOCUMENTS

| | | | |
|---|---|---|---|
| CN | 102753214 | A | 10/2012 |
| CN | 103492004 | A | 1/2014 |

(Continued)

*Primary Examiner* — Cris L. Rodriguez
(74) *Attorney, Agent, or Firm* — The Webb Law Firm

(57) ABSTRACT

Provided herein is a brake tower for a medical injection device, the brake tower having a proximal end, a distal end having a distal face, and a sidewall therebetween defining a longitudinal axis, and one or more protrusions arranged on and extending distally from the sidewall and/or the distal face. Also provided herein is a medical injection device including a brake tower.

17 Claims, 4 Drawing Sheets

(56) References Cited

U.S. PATENT DOCUMENTS

| | | | | |
|---|---|---|---|---|
| 2019/0247580 | A1 | 8/2019 | Schader et al. | |
| 2020/0282147 | A1* | 9/2020 | Quinn ............... | A61M 5/31575 |

FOREIGN PATENT DOCUMENTS

| | | | |
|---|---|---|---|
| CN | 106267470 | A | 1/2017 |
| CN | 207500376 | U | 6/2018 |
| CN | 114080249 | A | 2/2022 |

* cited by examiner

BRAKE TOWER WITH BIASING COMPONENTS AND MEDICAL INJECTION DEVICE INCLUDING THE SAME

CROSS-REFERENCE TO RELATED APPLICATIONS

This application is the United States national phase of International Application No. PCT/US2021/051690 filed Sep. 23, 2021, and claims priority to United States Provisional Application No. 63/083,617, entitled "Brake Tower with Biasing Components and Medical Injection Device Including the Same", filed Sep. 25, 2020, the entire disclosures of which are hereby incorporated by reference in their entirety.

BACKGROUND OF THE INVENTION

Field of the Invention

The present disclosure relates generally to components useful as replacements for helical coil springs for medical devices, and, in particular embodiments or aspects, to injection devices including a brake tower having a biasing component.

Description of Related Art

Medical injection devices often utilize resilient members, such as springs, placed between various components, to bias the components in order to ensure more accurate drug delivery. However, there are shortcomings to the use of current resilient members used in medical injection devices, such as a lack of control and load recovery. Accordingly, there is a need in the art for a more robust component to allow for greater load recovery.

SUMMARY OF THE INVENTION

Provided herein is a brake tower for a medical injection device, the brake tower having a proximal end, a distal end having a distal face, and a sidewall therebetween defining a longitudinal axis. The brake tower further includes one or more protrusions arranged on and extending distally from the sidewall and/or the distal face.

The one or more protrusions may be integral to the sidewall and/or the distal face. The one or more protrusions may include: a first portion extending distally from the distal face of the brake tower along the longitudinal axis, with the first portion having a proximal end and a distal end; and a second portion extending from the distal end of the first portion, the second portion arranged perpendicularly to the first portion. The second portion may extend radially inward from the distal end of the first portion. The one or more protrusions may be configured to buckle upon application of a force to the one or more protrusions along the longitudinal axis. The one or more protrusions may be formed from a polymer. The polymer may be a thermoplastic.

The one or more protrusions may be one or more staples. The one or more staples may include a plurality of longitudinally-extending portions, with each having a proximal end embedded in the distal face of the brake tower and a distal end spaced from the embedded proximal end, and a perpendicularly-extending portion attached to the distal ends of the longitudinally-extending portions. The proximal ends of the longitudinally-extending portions may be configured to embed in the distal face of the brake tower. The staple may be formed from a metal or a metal alloy. The proximal end, the distal end, and the sidewall may define a cylinder.

The distal end may have a larger circumference than the proximal end and/or the sidewall. The sidewall may define an interior that is at least partially hollow. The distal face may include two to ten protrusions arranged thereon.

Also provided herein is a medical injection device including a brake tower having a proximal end, a distal end having a distal face, and a sidewall therebetween defining a longitudinal axis, and one or more protrusions arranged on and extending distally from the sidewall and/or the distal face.

DESCRIPTION OF THE INVENTION

Figure 1:
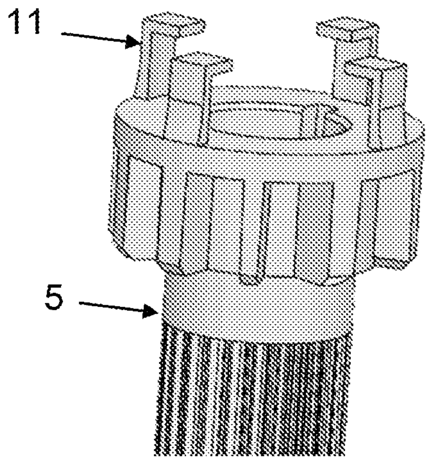
FIG. 1 shows a perspective view of a brake tower according to a non-limiting embodiment or aspect as described herein.

The use of numerical values in the various ranges specified in this application, unless expressly indicated otherwise, are stated as approximations as though the minimum and maximum values within the stated ranges are both preceded by the word "about". As used herein, the term "about" means the stated value ±10%. In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

Provided herein is a brake tower with a biasing component for use as a replacement for a spring in a medical device.

Turning to FIGS. 1-4, shown is a non-limiting embodiment or aspect of a brake tower 5 for a medical injection device. A brake tower can assume any useful configuration for use in a medical injection device. In non-limiting embodiments or aspects, brake tower 5 is cylindrical, and has a proximal end, a distal end, and a sidewall therebetween defining a longitudinal axis. In non-limiting embodiments or aspects, brake tower 5 is at least partially hollow, and the proximal end, distal end, and sidewall define an at least partially open interior that can receive one or more other components of a medical injection device, as will be described below. In non-limiting embodiments or aspects, interior of brake tower 5 includes one or more features for interacting, for example by reversible or irreversible locking, with a component received within the interior of the brake tower. For example, and without limitations, such features can include slots, tabs, recesses, and/or openings. Such features can, for example, prevent relative rotation between brake tower 5 and a component received within the brake tower interior, such as a brake tower core, a lead screw, and/or a piston rod.

In non-limiting embodiments or aspects, sidewall of brake tower 5 can include one or more splines or teeth configured to allow brake tower 5 to rotate when engaged by another component within a medical injection device, such as a setback member. In non-limiting embodiments or aspects, the one or more splines or teeth are configured to allow rotation of brake tower 5 in only a single direction.

In non-limiting embodiments or aspects, distal end of brake tower 5 is enlarged, for example by having a greater circumference than the proximal end. In non-limiting embodiments or aspects, distal end of brake tower 5 includes one or more features for interacting, for example by reversible or irreversible locking, with another component of a medical injection device, such as the housing. For example, and without limitations, such features can include one or more slots, tabs, recesses, and/or openings, and can prevent relative rotation between the brake tower and the component.

Brake tower 5 can be formed of any suitable material. In non-limiting embodiments or aspects, brake tower 5 is formed of a polymeric material, such as a plastic. In non-limiting embodiments or aspects, brake tower 5 is formed of a thermoplastic. In non-limiting embodiments or aspects, brake tower 5 is formed of a metal or a metal alloy.

With continuing reference to FIGS. 1-4, distal end of brake tower 5 includes a distal face. Brake tower 5 also includes one or more distally-extending protrusions 11. In non-limiting embodiments or aspects, one or more protrusions 11 are arranged on the sidewall and extend distally therefrom at the distal end of brake tower 5. In non-limiting embodiments or aspects, one or more protrusions 11 are arranged on and extend distally from distal face of brake tower 5. One or more protrusions 11 serve to bias a cartridge received within a medical injection device including the brake tower as described herein, minimizing shifting of the components and thereby ensuring a more accurate delivery of a composition from the cartridge. In a non-limiting embodiment or aspect, the distal face of brake tower 5 includes 2, 3, 4, 5, 6, 7, 8, 9, 10, or more protrusions 11. In one non-limiting embodiment or aspect, distal face of brake tower 5 includes two to four protrusions.

Figure 2:
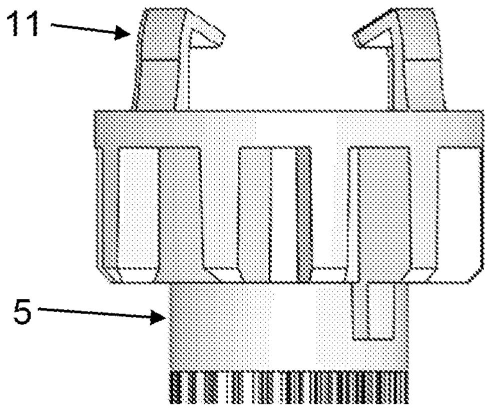
FIG. 2 shows a side view of a brake tower according to a non-limiting embodiment or aspect as described herein.

One or more protrusions 11 can take any suitable form for providing a biasing force against other components within a medical injection device (e.g., a cartridge or a cartridge housing). In non-limiting embodiments or aspects, for example as shown in FIGS. 1 and 2, one or more protrusions 11 can be molded plastic tabs. In non-limiting embodiments or aspects, one or more protrusions 11 are co-molded (e.g., by injection molding, compression molding, or any other suitable process) with brake tower 5, and thus are integrally formed with brake tower 5 and are formed of the same material. In non-limiting embodiments or aspects, one or more protrusions 11 are added after brake tower 5 is molded, for example with a suitable adhesive (e.g., hot melt), and can be of the same or a different material than brake tower 5. In such embodiments or aspects, one or more protrusions 11 can be formed of any suitable material, so long as the material provides the desired compressibility/expandability.

Figure 3:
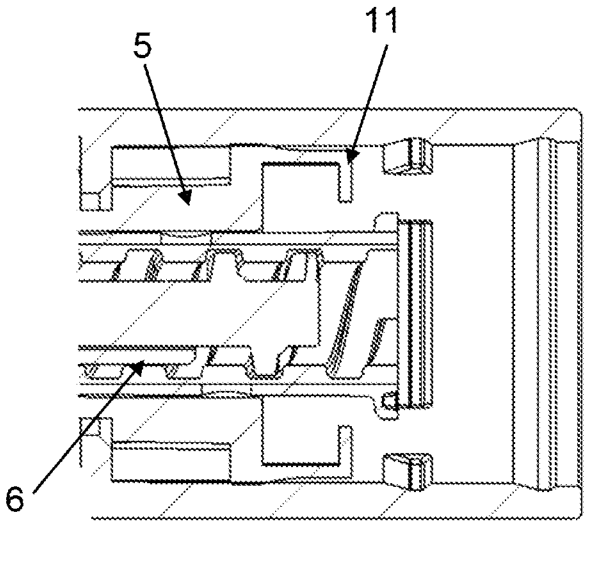
FIG. 3 is a partial cross-sectional view of a medical injection device including a brake tower according to a non-limiting embodiment or aspect as described herein, showing a pre-engagement position.
Figure 4:
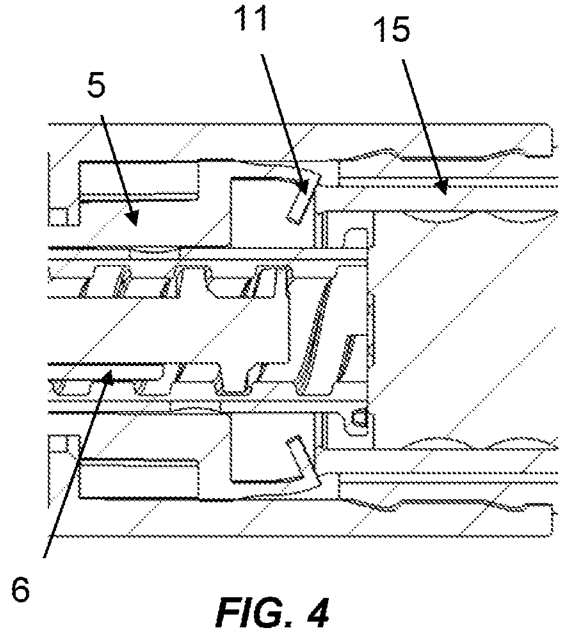
FIG. 4 is a partial cross-sectional view of a medical injection device including a brake tower according to a non-limiting embodiment or aspect as described herein, showing an engagement position.

With continuing reference to FIGS. 1-4, one or more protrusions 11 can assume any useful shape, configuration, and/or orientation on sidewall and/or distal face of brake tower 5. In non-limiting embodiments or aspects, one or more elastomeric protrusions have a circular shape or a polygon shape (e.g., a triangle, a quadrilateral, etc.). One or elastomeric protrusions 11 can also have a first height, measured from distal face of brake tower 5 distally along the longitudinal axis defined by the brake tower sidewall before brake tower 5 is pressed against another component (e.g., cartridge 15)(FIG. 3), and a second height, measured from distal face of brake tower 5 distally along the longitudinal axis defined by the brake tower sidewall after brake tower 5 is pressed against another component (e.g., cartridge 15) (FIG. 4). As shown in FIGS. 3 and 4, one or more protrusions 11 are deflected to bias the cartridge 15 such that the first height is larger than the second, deflected height. One or more protrusions 11 can be oriented randomly on sidewall and/or distal face of brake tower 5, or in a particular pattern.

In non-limiting embodiments or aspects, for example as shown in FIGS. 1 and 2, one or more protrusions 11 are configured in a substantially "L" shape, having a first portion that extends distally from the distal end of the brake tower 5 (e.g., from the sidewall or the distal face) along a longitudinal axis defined by the sidewall, and a second portion arranged at a distal end of the first portion and extending substantially perpendicular to the first portion. In non-limiting embodiments or aspects, second portion extends radially inward from the distal end of first portion. In non-limiting embodiments or aspects, for example as shown in FIG. 1, one or more protrusions 11 include an area of relative weakness, such as a seam, to allow one or more protrusions 11 to, upon being forced against another component (e.g., a cartridge 15), buckle or deflect. The biasing nature of one or more protrusions 11, based at least in part on the material from which one or more protrusions 11 are formed, can allow for one or more protrusions 11 to buckle while still applying a biasing force to the other component (e.g., a cartridge).

Figure 5:
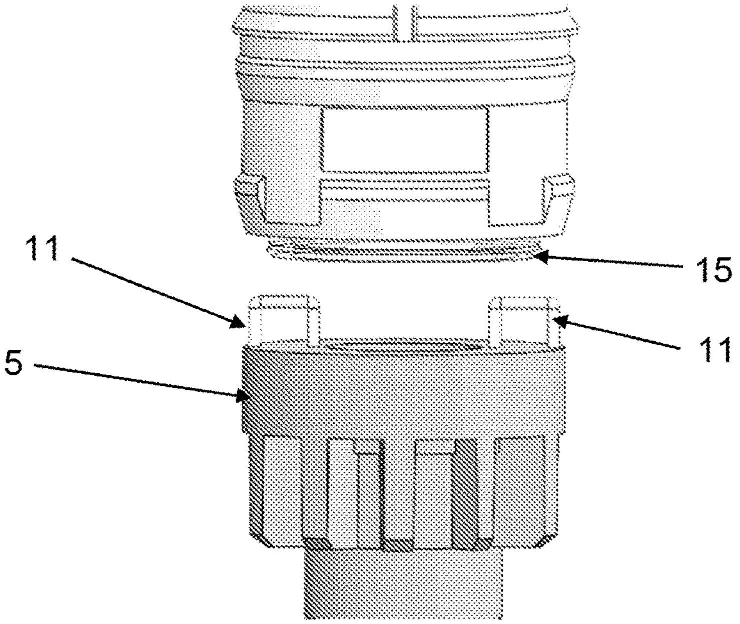
FIG. 5 is a side view of a brake tower as described herein according to a non-limiting embodiment or aspect.
Figure 6:
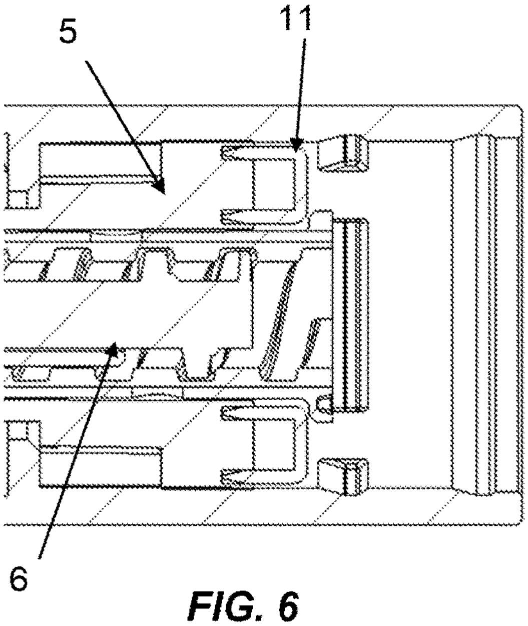
FIG. 6 is a partial cross-sectional view of a medical injection device including a brake tower according to a non-limiting embodiment or aspect as described herein, showing a pre-engagement position.
Figure 7:
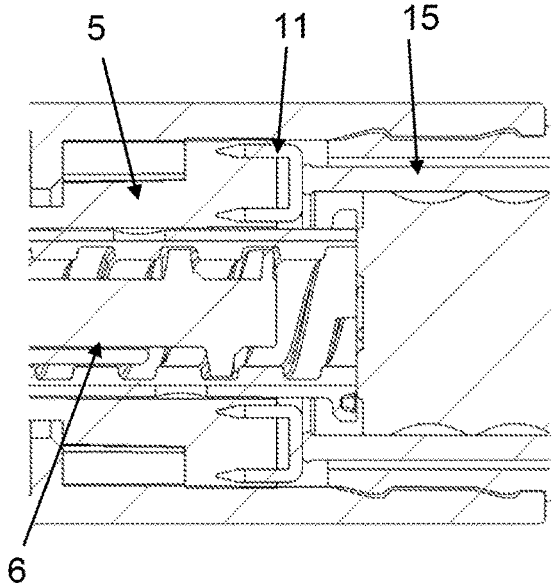
FIG. 7 is a partial cross-sectional view of a medical injection device including a brake tower according to a non-limiting embodiment or aspect as described herein, showing an engagement position.

Turning to FIGS. 5-7, in a non-limiting embodiment or aspect, one or more protrusions 11 can be one or more staples extending distally from the distal face of brake tower 5. Staples can be formed of any suitable material, but in a preferred, non-limiting embodiment or aspect, the staples are metal or a metal alloy. Staples can be attached to brake tower 5 following molding of brake tower 5. Staples can be configured to assume any suitable shape. In non-limiting embodiments or aspects, staples include two longitudinally-extending portions, each having a proximal end configured to be embedded in the distal face of brake tower 5 and a distal end spaced from the proximal end. Staples can also include a perpendicular portion attached to the distal ends of the longitudinally-extending portions, as shown in FIG. 3. Proximal ends of the staples can be configured to reduce the force necessary to embed the staples into the distal face of brake tower 5 when distal face of brake tower 5 is pressed against another component of a medical injection device (e.g., cartridge 15). For example, and without limitation, each of the proximal ends of staples can form a point. Staples can be attached at any suitable depth of penetration into distal face of brake tower 5. As shown in FIG. 6, prior to engagement of the one or more protrusions 11 with the cartridge 15, the one or more protrusions 11 extend a first distance from the brake tower 5. As shown in FIG. 7, upon engagement of the one or more protrusions 11 with the cartridge 15, the one or more protrusions 11 are pushed further into the brake tower 5 such that the one or more protrusions 11 extend a second distance from the brake tower 5, which is smaller than the first distance.

Figure 8:
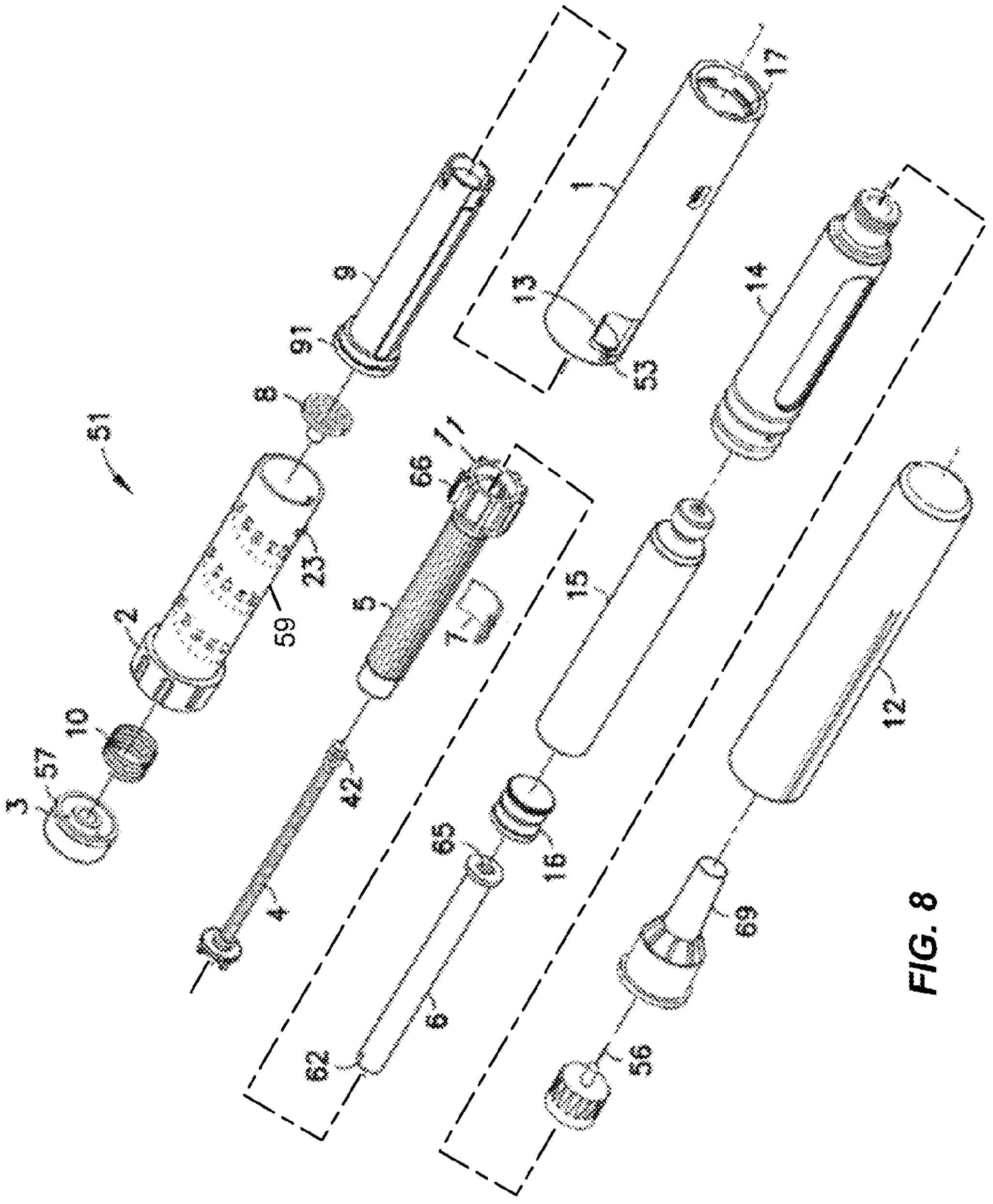
FIG. 8 is an exploded view of a medical injection device including a brake tower with a biasing component according to a non-limiting embodiment or aspect as described herein.
Figure 9:
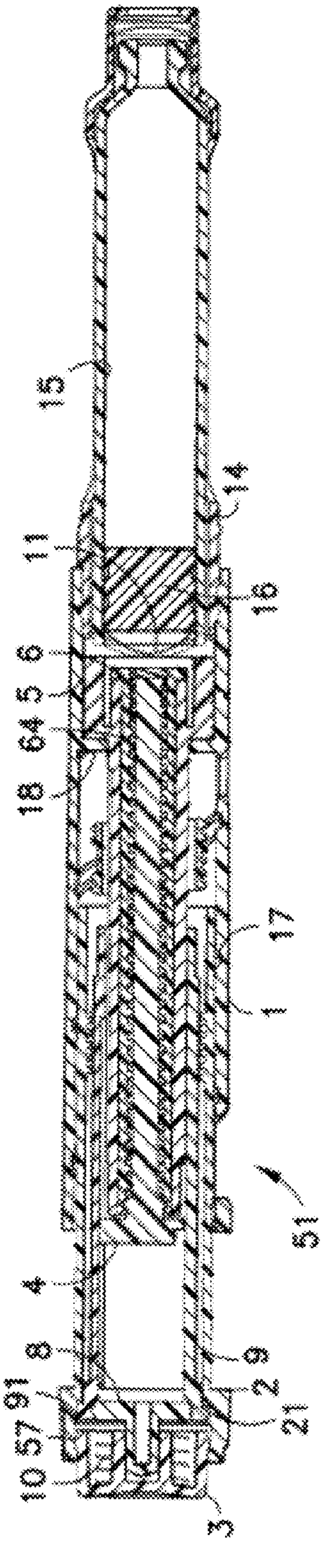
FIG. 9 is a cross-sectional view of a medical injection device including a brake tower with a biasing component according to a non-limiting embodiment or aspect as described herein.

Also provided herein is a medical injection device including a brake tower with one or more protrusions as described above. Such devices, such as injection pens, are described in U.S. Pat. No. 9,421,334, incorporated herein by reference in its entirety. With reference to FIGS. 8 and 9, shown are an exploded (FIG. 8) and cross-sectional (FIG. 9) view of an injection pen 51 for delivery of a composition to a user. As shown, injection pen 51 includes a pen upper body or housing 1, which houses a plurality of dose setting and injection components. Pen upper body 1 is connected to a cartridge housing 14, which houses cartridge 15. Injection pen 51 can also include a lower pen cap 12 to cover the cartridge 15 and cartridge housing 14 when injection pen 51 is not in use. As shown, injection pen 51 can include a dose set knob 2 that includes a knob-like portion that is rotated by a user to set a desired dose. Dose set knob 2 can also include a plurality of numerals, corresponding to a number of dosage units that is visible through a window 13 provided on pen upper body 1. A user rotates dose set knob 2 until the desired dose is visible in window 13. Pen upper body 1 can include an arrow or other indicator 53 to precisely indicate the set dose. Once the desired dose is set, a user presses a button 3 until the set dosage amount is completely injected. An outer shield 69 can cover a needle 56 to prevent accidental needle sticks upon removal of the lower pen cap 12.

Injection pen 51 can include push button 3, provided at a proximal end, closest to a user and farthest from needle 56, of pen upper body 1. Push button 3 can include an annular bead or rim 57 that engages with a corresponding annular groove (not shown) provided on the internal surface of dose set knob 2. The annular rim and groove connection can be a friction fit that maintains push button 3 in a biased position on dose set knob 2 under the force of a button spring 10, but allows push button 3 to be pushed into dose set knob 2 for injecting a set dose. The interior of push button 3 can accommodate a setback bearing insert 8 that rests on an internal surface at a proximal end of a setback member or driver 9. Push button 3 can be designed to rotate freely on setback bearing insert 8.

Setback member or driver 9 can be a cylindrical member, coaxial with and surrounded by dose set knob 2. Setback member 9 can be provided co-axially around brake tower 5 as described above. Brake tower 5 can be axially and rotatably fixed to pen upper body 1. In non-limiting embodiments or aspects, brake tower 5 co-axially surrounds a piston rod 6. Piston rod 6 can include a set of keys (not shown) that engage a slot (not shown) internal to brake tower 5 (as described above) to rotatably lock piston rod 6 to brake tower 5. Piston rod 6 can include a plurality of threads (not shown) provided on the interior surface thereof. Piston rod 6 can co-axially surround a lead screw 4 that includes a series of threads 42 at least at its distal end. Lead screw threads 42 can be configured to be in threaded engagement with the internal threads (not shown) provided on the interior of piston rod 6. Due to its threaded engagement with lead screw 4, piston rod 6 can be moved into cartridge 15 during injection to press on a stopper 16 provided inside cartridge 15 to expel a dose of medication.

With reference to the present disclosure, injection pen 51 includes brake tower 5 as described above. Brake tower 5 includes a distal face including one or more protrusions as described above, positioned between brake tower 5 and cartridge 15 to bias the cartridge 15 in a distal direction to prevent any movement of the cartridge 15 during injection, and thus ensuring that an accurate dose is injected.

With regard to the embodiment illustrated in FIGS. 1-4, when injection pen 51 including brake tower 5 as shown is assembled, the distal face of brake tower 5 is forced against cartridge 15. As a result, one or more protrusion are deformed, for example, as shown in FIG. 4, by buckling. By virtue of the resilient material from which the one or more protrusions are formed, the protrusions maintain contact with and a biasing force against cartridge 15, preventing movement of the cartridge during an injection and ensuring that an accurate dose is injected.

With regard to the embodiment illustrated in FIGS. 5-7, when injection pen 51 including brake tower 5 as shown is assembled, the distal face of brake tower 5 is forced against cartridge 15. As a result, one or more staples are embedded further in the distal face of brake tower 5. However, one or more staples do not embed further than that required to allow for brake tower 5 and cartridge 15 to abut each other within the upper body 1 of the injection pen 51. Perpendicular portion of the one or more staples abuts a proximal end of cartridge 15, preventing movement of the cartridge during an injection and ensuring that an accurate dose is injected.

Following assembly, and when injection pen 51 is ready to be used, a dose for drug delivery can be set. To set a dose using injection pen 51 as described herein, a user rotates the knob portion of dose set knob 2 relative to pen upper body 1. An outer surface 59 of the dose set knob 2 can include a thread 23, which is in threaded engagement with a plurality of threads 17 provided on the internal surface of the pen upper body 1, as shown in FIGS. 8 and 9. Accordingly, as dose set knob 2 is rotated relative to pen upper body 1, dose set knob 2 screws or advances a distance out of pen upper body 1, as shown in FIG. 9. Dose set knob 2 can include an annular shoulder or rim 21 on the interior surface thereof near the proximal end, as shown in FIG. 9. This annular shoulder 21 can engage with an enlarged portion or head 91 of setback member 9, as shown in FIG. 9. Annular shoulder 21 of dose set knob 2 can include a series of teeth or ridges 22 that engage with a plurality of similarly shaped teeth or ridges (not shown) provided on enlarged head 91 of setback member 9. Dose set knob teeth 22 and setback member teeth can extend in opposite axial directions. During dose setting, dose set knob 2 can be free to rotate with respect to setback member 9 in both clockwise and counter-clockwise directions. As this occurs, the plurality of teeth or ridges 22 on dose set knob 2 can slip past the teeth provided on head portion 91 of setback member 9, thus providing a tactile signal or clicking noise to indicate the setting of a dosage amount.

With regard to the injection mechanism, as described above, lead screw 4 can include a plurality of threads 42 at its distal end that are in threaded engagement with a plurality of threads 64 that can be provided along the entire length of a hollow piston rod 6 as shown in FIG. 8. Piston rod 6 can be held non-rotatably with respect to pen upper body 1 due to a non-rotatable coupling with brake tower 5, which can be held axially and rotatably fixed with respect to the pen upper body 1. Piston rod 6 can include a key or set of keys 62 at its distal end that engage with a slot (not shown) provided on the internal surface of the brake tower 5 to prevent relative rotation therebetween while permitting piston rod 6 to move axially with respect thereto. Threads 42 of lead screw 4 can include a flat portion (not shown) corresponding to a flat portion 65 of piston rod 6, such that axial movement of the lead screw during dose setting does not result in axial movement of the piston rod 6. Accordingly, rotation of lead screw 4 during injection of a dose can cause the threads 42 of lead screw 4 to engage threads 64 of the piston rod 6, thereby axially moving piston rod 6. Because piston rod 6 can be non-rotatable with respect to body 1, as lead screw 4 is caused to rotate during injection, as described above due to its rotational coupling setback member 9, piston rod 6 through its threaded engagement with lead screw 4 can be caused to move in the distal direction to press against stopper 16 provided in cartridge 15, thus expelling a liquid medication therefrom.

Although the devices have been described in detail for the purpose of illustration based on what is currently considered to be the most practical and preferred embodiments, it is to be understood that such detail is solely for that purpose and that the systems and methods are not limited to the disclosed embodiments, but on the contrary, is intended to cover modifications and equivalent arrangements that are within the spirit and scope of the appended claims. For example, it is to be understood that the present systems and methods contemplate that, to the extent possible, one or more features of any embodiment can be combined with one or more features of any other embodiment.

The invention claimed is:

1. A brake tower for a medical injection device, comprising:
- a proximal end, a distal end having a distal face, and a sidewall therebetween defining a longitudinal axis; and
- one or more protrusions arranged on and extending distally from the sidewall and/or the distal face wherein the one or more protrusions comprise:
  - a first portion extending distally from the distal face of the brake tower along the longitudinal axis, the first portion having a proximal end and a distal end; and
  - a second portion extending from the distal end of the first portion, the second portion arranged perpendicularly to the first portion.

2. The brake tower according to claim 1, wherein the one or more protrusions are integral to the sidewall and/or the distal face.

3. The brake tower according to claim 1, wherein the second portion extends radially inward from the distal end of the first portion.

4. The brake tower according to claim 1, wherein the one or more protrusions are configured to buckle upon application of a force to the one or more protrusions along the longitudinal axis.

5. The brake tower according to claim 1, wherein the one or more protrusions comprise a polymer.

6. The brake tower according to claim 5, wherein the polymer comprises a thermoplastic.

7. The brake tower according to claim 1, wherein the one or more protrusions comprise one or more staples.

8. The brake tower according to claim 7, wherein the one or more staples comprise:
- a plurality of longitudinally-extending portions, each having a proximal end embedded in the distal face of the brake tower and a distal end spaced from the embedded proximal end; and
- a perpendicularly-extending portion attached to the distal ends of the longitudinally-extending portions.

9. The brake tower according to claim 8, wherein the proximal ends of the longitudinally-extending portions are configured to embed in the distal face of the brake tower.

10. The brake tower according to claim 7, wherein the staple comprises a metal or a metal alloy.

11. The brake tower according to claim 1, wherein the proximal end, the distal end, and the sidewall define a cylinder.

12. The brake tower according to claim 1, wherein the distal end has a larger circumference than the proximal end and/or the sidewall.

13. The brake tower according to claim 1, wherein the sidewall defines an interior that is at least partially hollow.

14. The brake tower according to claim 1, wherein the distal face comprises two to ten protrusions arranged thereon.

15. A medical injection device comprising:
- a housing having a distal end and a proximal end;
- a brake tower comprising a proximal end, a distal end having a distal face, and a sidewall therebetween defining a longitudinal axis, and one or more protrusions arranged on and extending distally from the sidewall and/or the distal face;
- a cartridge received within the housing distally of the brake tower and holding a composition therein;
- a cartridge housing received within the housing distally of the brake member and configured to hold the cartridge therein;
- an injection needle at a distal end of the housing and in fluid communication with the cartridge; and
- an actuation member at a proximal end of the housing, the actuation member configured to actuate the medical injection device to deliver the composition through the injection needle,
- wherein the one or more protrusions arranged on and extending distally from the sidewall and/or the distal face of the brake tower bias the cartridge distally,
- wherein the one or more protrusions comprise:
  - a first portion extending distally from the distal face of the brake tower along the longitudinal axis, the first portion having a proximal end and a distal end; and
  - a second portion extending from the distal end of the first portion, the second portion arranged perpendicularly to the first portion.

16. The medical injection device of claim 15, wherein the one or more protrusions comprise one or more staples.

17. A brake tower for a medical injection device, comprising:
- a proximal end, a distal end having a distal face, and a sidewall therebetween defining a longitudinal axis; and one or more protrusions arranged on and extending distally from the sidewall and/or the distal face, wherein the one or more protrusions comprise one or more staples.

* * * * *